United States Patent [19]

Iizuka

[11] Patent Number: 5,370,457
[45] Date of Patent: Dec. 6, 1994

[54] THERMOMECHANICAL ANALYZER

[75] Inventor: Nobuo Iizuka, Tokyo, Japan

[73] Assignee: Seiko Instruments Inc., Tokyo, Japan

[21] Appl. No.: 134,846

[22] Filed: Oct. 12, 1993

[30] Foreign Application Priority Data

Oct. 12, 1992 [JP] Japan ................... 4-273024

[51] Int. Cl.⁵ .............................................. G01N 3/18
[52] U.S. Cl. ........................................ 374/51; 374/49; 73/818; 73/826
[58] Field of Search ............... 374/51, 49, 46; 73/818, 73/826

[56] References Cited

U.S. PATENT DOCUMENTS

| | | | |
|---|---|---|---|
| 2,545,482 | 3/1951 | Manjoine et al. | 374/49 |
| 2,699,060 | 1/1955 | Safford | 374/51 |
| 2,754,675 | 5/1956 | More | 374/51 |
| 2,763,149 | 9/1956 | Long et al. | 374/49 |
| 4,837,776 | 6/1989 | Poll | 374/51 |
| 5,249,471 | 10/1993 | Kizaki et al. | 73/826 |

FOREIGN PATENT DOCUMENTS

| | | | |
|---|---|---|---|
| 0012400 | 6/1980 | European Pat. Off. | 374/51 |
| 2014766 | 10/1971 | Germany | 374/49 |
| 0399617 | 3/1943 | Italy | 374/51 |
| 0230034 | 11/1985 | Japan | 374/49 |
| 0130850 | 6/1986 | Japan | 374/49 |
| 0187237 | 8/1987 | Japan | 73/818 |
| 0274033 | 11/1989 | Japan | 374/49 |
| 0068836 | 3/1991 | Japan | 374/49 |
| 403251752 | 11/1991 | Japan | 374/51 |
| 404235329 | 8/1992 | Japan | 73/826 |
| 0291127 | 1/1971 | U.S.S.R. | 374/51 |

Primary Examiner—Diego F. F. Gutierrez
Attorney, Agent, or Firm—Spensley Horn Jubas & Lubitz

[57] ABSTRACT

A thermomechanical analyzer including a vertical probe secured to a probe holding bar. The probe and the probe holding bar are coupled to a force generator for supplying a force in the vertical direction, a differential transformer for detecting the degree of movement in the vertical direction, and two supports each composed of a pair of wires and a coil spring in the horizontal direction. The force generator is located between the two supports. Thus, the movement of the probe holding bar in a radial direction is controlled. The size of the instrument becomes compact. As the movement of the probe holding bar in a radial direction is controlled to be very small, the moving range of the probe becomes broader and a large sample deformation can be measured with precision.

8 Claims, 4 Drawing Sheets

THERMOMECHANICAL ANALYZER

BACKGROUND OF THE INVENTION

The invention relates to a thermomechanical analyzer.

In a conventional thermomechanical analyzer as shown in FIG. 4, strain of a sample is detected by detecting a displacement of a probe using a balance beam, while a stress is applied to the sample from the end of the balance through the probe. The structure is explained as follows.

A sample 1 is set upon a bottom of a cylindrical datum tube 2 having a sole. Around the bottom of the cylindrical datum tube 2 for supporting the sample 1, an electric furnace 20 is provided for heating the sample 1 according to a predetermined temperature program. The temperature of the furnace 20 is controlled by a temperature controller 21. The electric furnace 20 can be moved either upwards or downwards (the direction of the arrow B) by a mechanism (not shown therein). A hole 6a is formed at a base frame 6 and the datum tube 2 is inserted into the hole 6a with a space between tube 2 and the edge of hole 6a.

A flange is formed at the upper top portion of the datum tube 2 and overhung around the outer periphery of thereof. And the datum tube 2 is held by the flange which overhangs a hole in a datum tube support 18. The datum tube support 18 is slidably mounted to two pieces of guide bars 16 fixed to the base frame 6 vertically, through respective guide bearings. Furthermore, the top of a micrometer 19 contacts the bottom of the datum tube support 18. Through the movement of the micrometer (dial) 19, datum tube 2 can be slid and set at a designated position (the direction of the arrow A of the figure). The head of the probe 3 is vertically contacted with the sample 1 which is mounted in the datum tube 2. A core 5 made of magnetic materials is fixed upon the bar shaped probe 3, and surrounded by a differential transformer 4. The differential transformer 4 is supported by a differential transformer support 15 which is firmly fixed with the end of the guide bar 16. The signal from the differential transformer 4 is inputted to a detecting circuit 23.

The micrometer is provided for correcting the changes of the relative position between the core 5 and the differential transformer 4, which occurs depending on the length of the sample 1. In case that the sample 1 is longer, the datum tube support 18 is lowered so that the datum tube 2 is lowered by action of the micrometer 19.

Furthermore, a fulcrum base 28 is provided on the base frame 6 and supports a balance arm (beam) 26 at the top through the fulcrum 27 provided on the top thereof. The fulcrum 27 is for supporting the balance arm 26 to pivot freely. At an end 26a of the balance arm 26, there is provided a core joint 30 which is connected to the probe 3 or the core 5. And a force generator 7 is provided at the other end 26b. The force generator 7 comprises a magnet 7a and a coil 7b. The coil 7b is fixed on the balance arm 26 and the magnet 7a is fixed on the base frame 2 through a magnet base 29. The force generator 7 is structured as shown in FIG. 5; a narrow circular groove 7c is vertically formed on the magnet 7a, and the circular coil 7b is inserted into the groove 7c.

The coil 7b of the force generator 7 is electrically connected to a force generator circuit 22. According to the electric power from the force generator circuit 22, the coil 7b pulls or pushes the other end 26b of the balance arm 26. The electric power from the force generator circuit 22 is controlled by a CPU 24.

With above mentioned structure, a thermomechanical analysis of the sample is performed as follows: the sample 1 can be heated according to a predetermined temperature program, and a prescribed stress is applied to the sample 1 via the balance arm 26 and the probe. The stress is originally generated by the force generator 7 provided at the end of the balance are 26. The degree of the deformation (strain) of the sample 1 due to the applied stress is detected by the detecting circuit 23 through the change in relative location between the core 5 and the differential transformer 4.

According to the above structure, coil 7b of the force generator 7 equipped at the end 26b of the balance arm 26 moves along an arc centered on the fulcrum 27 as shown in FIG. 5 by arrow D. In particular, the lower end 7d of the coil 7b moves along a circular arc as shown by arrow Dd in FIG. 5. The arrow Dd is drawn in exaggeration in terms of its shape compared to the actual movement. And a clearance (gap) between the coil 7b and the groove 7c of the magnet 7a is made very narrow in order to fully demonstrate the function of the force generator 7. Accordingly, the lower end 7d of the coil 7b may collide with the side wall of the groove 7c of the magnet 7a, when the end of the balance arm 26 shifts slightly upwards or downwards. For this reason, the shift range of the balance arm 26 and probe 3 is very limited. The range of the shift allowance (D2) of the lower end 26b of the balance arm 26 is shown in FIG. 5.

As the gap size between the coil 7b and the groove 7d wall of the magnet 7a varies according to the shift of the balance arm 26 (direction D), the relationship between the electric power to be supplied to the coil 7b from the force generation circuit 22 and the force (stress) to be generated by the force generator 7 varies in relation to the shift and is not linear.

Moreover, the top end 26a of the balance arm 26 which supports the probe 3 moves in an arc. Therefore, the probe 3 does not shift correctly in the vertical direction.

In order to compensate this above appearance, in the prior art the balance arc 26 was made longer and had to be instituted in the horizontal direction; consequently, the instrument itself tended to be bigger. And the balance portion must be highly elaborate, and it needs to be assembled carefully.

SUMMARY OF THE INVENTION

In order to solve the above-mentioned problems, the thermomechanical analyzer of the invention comprises a probe having a perpendicular contact with the sample at the top for detecting a strain of the sample; a probe holding-bar for holding the probe in perpendicular at the top; a force generator formed with a magnet and a coil fixed at the probe holding-bar; a magnet holder for supporting the force generator; a differential transformer core fixed on the probe holding-bar; a differential transformer fixed around the differential core; a bendable pair of wires horizontally fixed onto the force generator holder at a certain angle between said wires on flat plane in perpendicular against the longer direction of the probe holding-bar for supporting the probe holding-bar; a bendable, elastic coil formed on the same horizontal plane as the plane of the wires, and fixed on the magnet holder, for supporting the probe holding-bar; and a furnace for heating the sample.

The structure in this invention can be compactly assembled and operated, because the sample, the probe for applying the stress to the sample and for detecting the strain of the sample, the core and the differential transformer for detecting the shift of the probe, and the force generator for generating the force (stress) which inputs on the sample are linearly instituted. The probe and the probe holding-bar for holding the probe are linearly instituted, and are connected in separable state to each other by the probe joint. The radial shift of the probe holding-bar can be avoided, because the probe holding bar is held by the bendable pair of the wires which are fixed to the inside wall of the force generator holder on the horizontal flat plane and have a certain angle each other, and held by the bendable, elastic coil spring which are fixed to the inside wall of the force generator holder. That is, the probe and the probe holding-bar are held and moved vertically.

Further, the probe holding-bar moves along an arc as shown by arrow E in FIG. 3. The wires are made of a bendable material, and one end of each wire is rotatably supported at the inner wall of the force generator holder. And the other end of each wire is fixed to the probe holding-bar through the holder ring. That is, when the probe holding-bar is moved up and down, the probe holding-bar also shifts slightly in a radial direction. As the rotating movement direction (tangent line) of the wire at the neutral position is vertical, the probe holding-bar tends to shift less than that in the prior art, even if the probe holding-bar moves more or less in a perpendicular direction. This is to say, the range $d_1$ of allowance change (in vertical distance) of the probe holding-bar in the present invention is bigger than that in the prior art. $d_1$ is about three times as big as $d_2$.

The relation between the force generated by the force generator and the electric power supplied to the force generator from the force generating circuit changes almost nil, since the gap between the coil and the groove wall of the magnet changes almost nil. That is, its linearity is improved in the present invention.

DESCRIPTION OF THE PREFERRED EMBODIMENTS

The embodiment of the present invention will be described in the following with reference to the figures.

Figure 1:
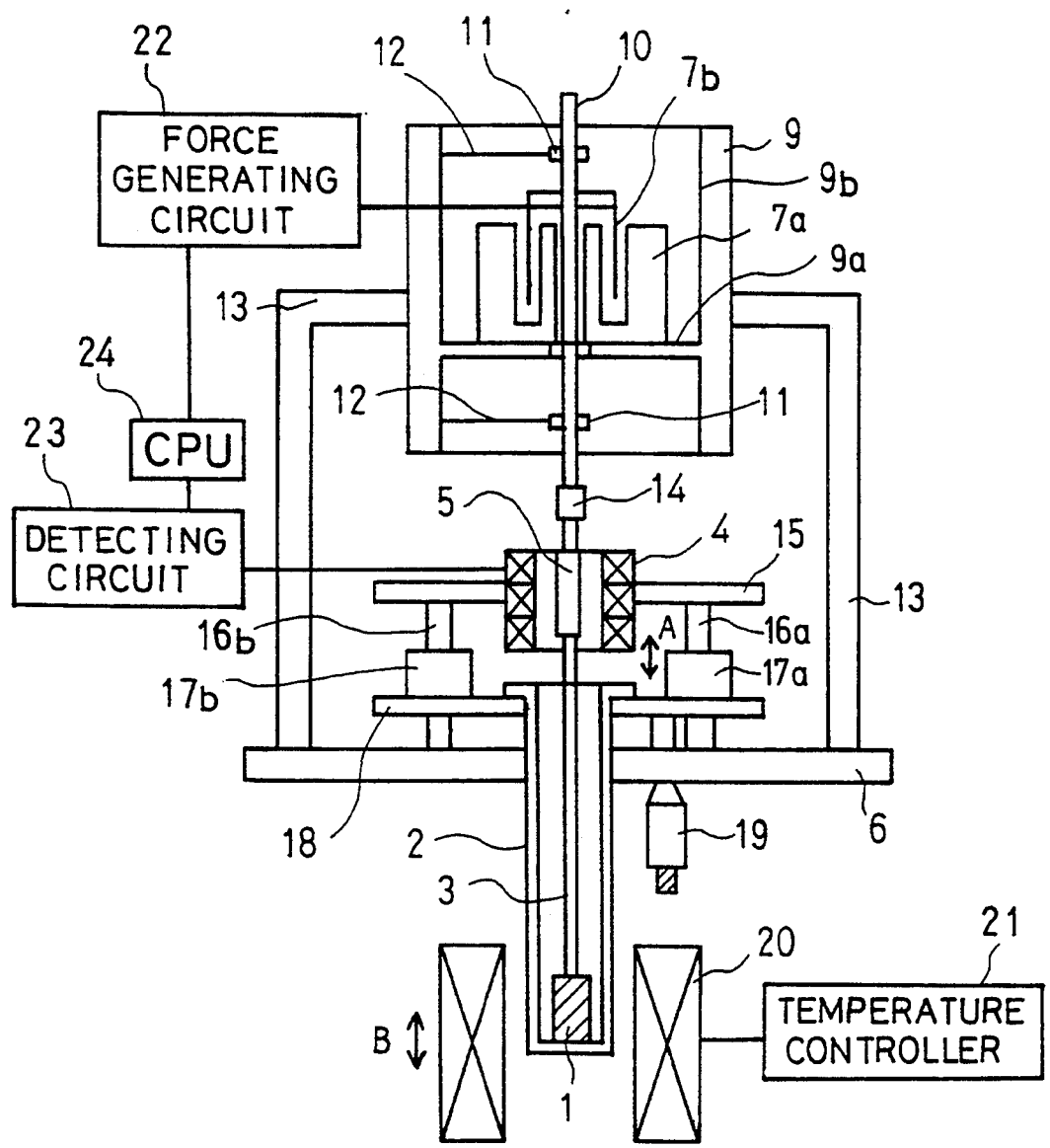
FIG. 1 is a sectional view of the embodiment of the invention.
Figure 4:
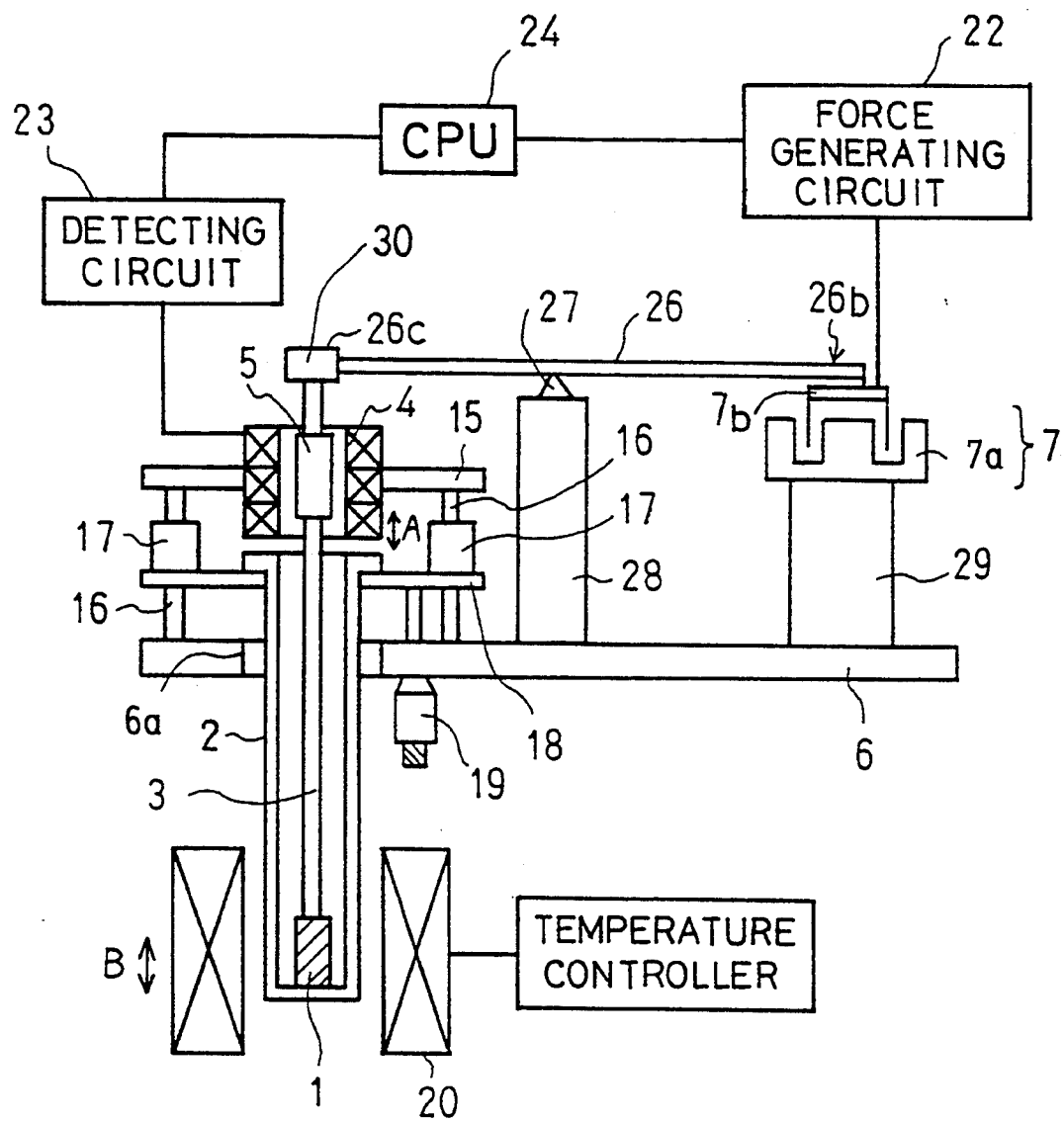
FIG. 4 is a sectional view of the prior art.
Figure 5:
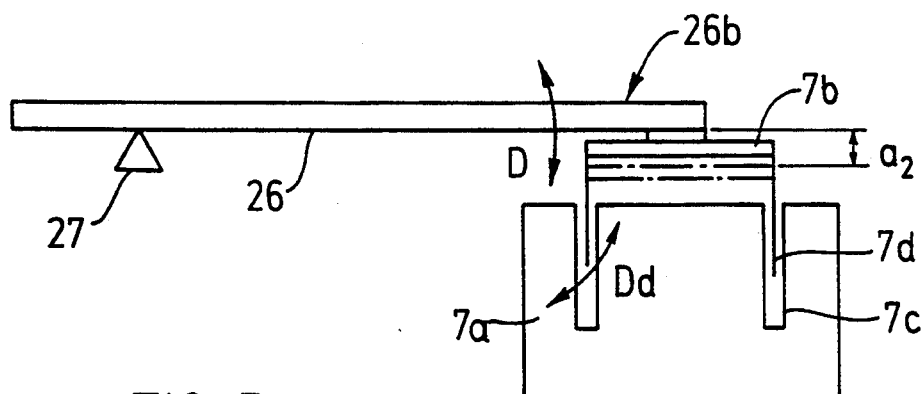
FIG. 5 is a sectional view showing the force generator 7 and its operations of the prior art.

In FIG. 1, a sample 1, a datum, or reference, tube 2, a differential transformer 4, a core 5, a base frame 6, a differential transformer support 15, a guide bar 16, a guide bearing 17, a datum tube support 18, a micrometer 19, an electric furnace 20, and a temperature controller 21 are essentially the same as those described above with reference to FIG. 4; therefore further explanation is hereunder abbreviated.

Figure 3:
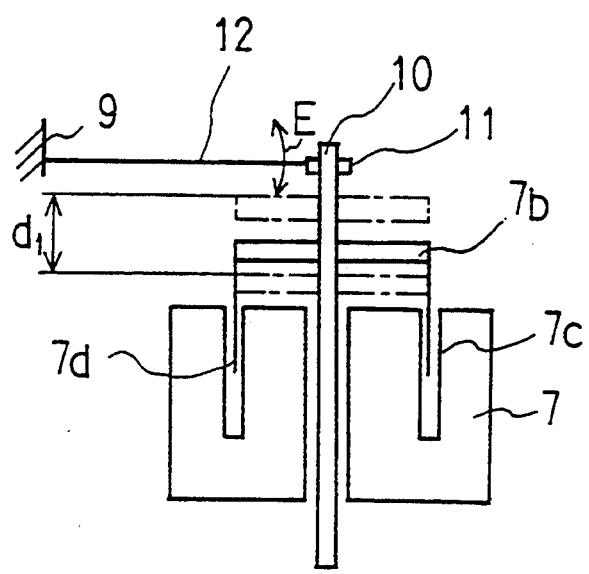
FIG. 3 is a sectional view showing the force generator 7 and its operations of the invention.

A probe holding-bar 10 is attached to the upper end of the probe 3 vertically with a probe joint 14. A force generator 7a, 7b is provided at the probe holding-bar 10, and comprises a circularly wound coil 7b fixed firmly onto the probe holding bar 10, and a magnet 7a which is circular and has a narrow groove 7c (FIG. 3) for inserting the coil 7b therein with a narrow clearance between the groove 7c and the coil 7b. The magnet 7a has a through hole at the center thereof so that the probe holding bar 10 passes through the hole. The hole of the magnet 7a has a bigger diameter than the probe holding-bar 10 so as to avoid contact between the probe holding-bar 10 and the magnet 7a. The coil 7b of the force generator is connected to a force generator circuit 22 and generates a force controlled by a CPU 24 to be supplied to the probe holding-bar 10, and then puts a predetermined stress on the sample 1 thereby.

Figure 6:
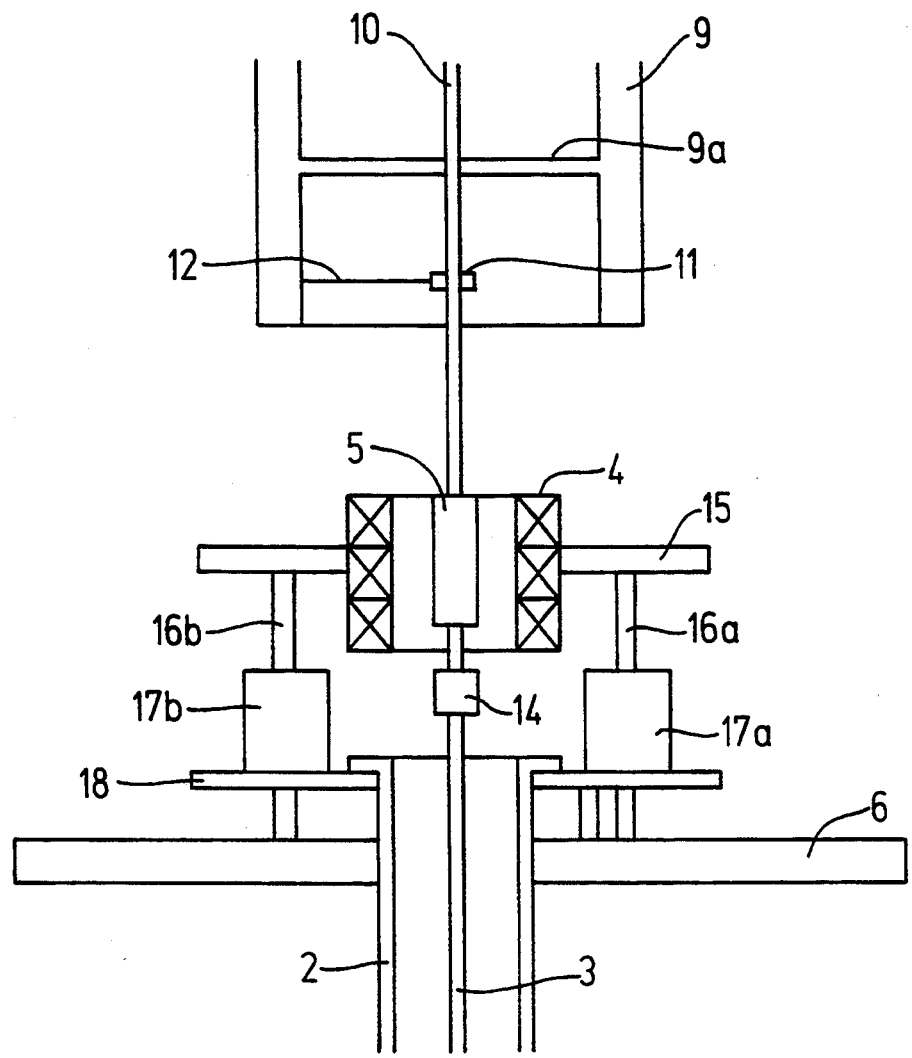
FIG. 6 is a detail sectional view of an alternative embodiment of the invention.

Further, a displacement detector comprising the core 5 and the differential transformer 4 (a differential transformer may generally include a core) is provided for detecting the strain of the sample 1. A signal from the displacement detector is inputted into a detecting circuit 23 and then operation-and-data-processed by the CPU 24. The location of the core 5 may not be limited to that on the probe 3 only, but may be on the probe holding-bar 10, as shown in FIG. 6, or the probe joint 14. In the latter case, the differential transformer 4 should be located around core 5.

Figure 2:
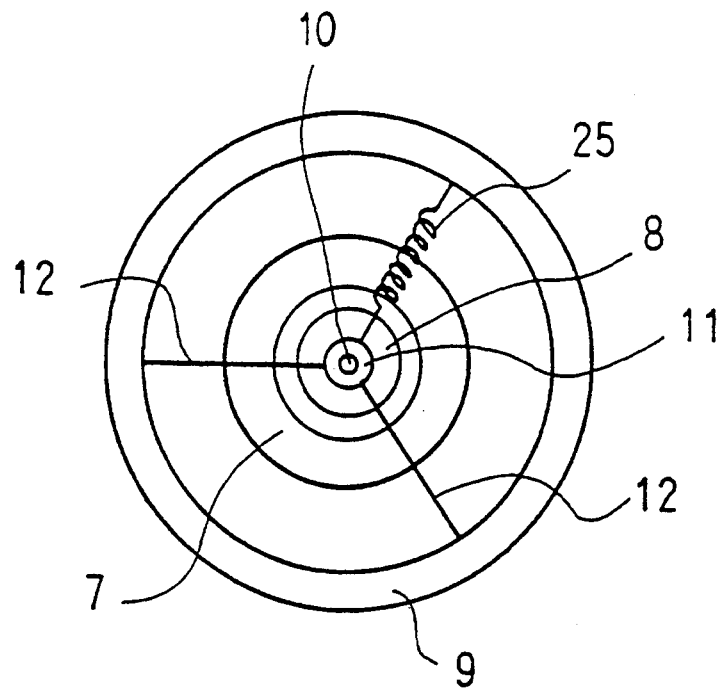
FIG. 2 is a plane view of the mechanism for horizontally holding the probe holding-bar 10.

The magnet 7a of the force generator 7 is fixed/on the magnet holder 9. The magnet holder 9 is also formed with a through hole so that the probe holding-bar 10 passes through the hole. The magnet holder 9 is fixed on the base frame 6 via the magnet holder support 13. The magnet holder 9 is formed with a magnet placing plate 9a for placing the magnet 7a and a wire-fixing side wall 9b for installing a mechanism for restraining the probe holding-bar 10 against horizontal movement (radial direction). As mentioned above, the mechanism for horizontally holding the probe holding-bar 10 comprises a pair of wires 12 formed at a certain angle to each other, as shown in FIG. 2, a coil spring 25 formed to oppose the pair of the wires, and a holder 11 for connecting wires 12 and spring 25 to the probe holding-bar 10. The pair of wires 12, the coil spring 25 and the holder 11 are formed on a plane perpendicular to the center axis of the probe holding-bar 10.

The angles between the wires 12 and the coil spring 25 are preferably 120°, but should not be limited to 120°.

The wires 12 are bendable and elastic, and are formed in the shape of straight springs. Coil spring 25 supplies a slight tension force and pulls the pair of wires 12 with small force.

Another mechanism for horizontally holding the probe holding-bar 10 is provided at the wire-fixing side wall 9b beneath force generator 7. The pairs of wires 12 that are formed above and below force generator 7 preferably extend in the same directions and in the same patterns when viewed in plan. The reason is as follows. When the probe 3 and the probe holding-bar 10 are displaced up and down due to the strain of the sample 1, the probe holding-bar 10 shifts slightly in the horizontal direction (radial direction about its axis) as explained before. Of course, the amount of this shift is less than that in the prior art. Wires 12 and spring 25 of one mechanism extend in different directions from those of the other mechanism, the directions of the horizontal shifts due to the two mechanisms are different from each other, and therefore, the probe holding-bar 10 and the probe 3 become slanted. The probe holding-bar 10 is always kept in the perpendicular position by the two (above and below) mechanisms for horizontally holding the probe holding-bar 10.

As the probe 3 and the probe holding-bar 10 are always kept in the perpendicular position by the above structure, the wires 12 and coils 25 will bend. Therefore, in measuring, the force controlled by CPU 24 tends to hold the wires 12 and coils 25 in the horizontal position.

Next, the operation procedure of the thermomechanical analysis of the sample 1 using this invention will be explained hereinafter. The sample 1 is placed on the bottom of the datum tube 3 on the datum tube support 18, and the datum tube 2 can be moved in the direction A by the micrometer 19, until the top head of the probe contacts the sample 1 while the force generator 7 is generating an upward force to the probe holding-bar 10 so that the wires 12 and the coil springs 25 can be held in horizontal flat.

Then, the electric furnace 20 is moved to a predetermined position on the direction B. Until this time, the top head of the probe 3 has a contact with the surface of the sample 1 with no load. And then, the force generating circuit 22 outputs a predetermined current (electric force to the force generator 7 by a controlling signal from the CPU 24. The current from the force generating circuit 22 can be a constant (DC) current or a current having a time function. Then, the magnetic field is generated by the coil 7b of the force generator 7 according to the current thereof. The stress (force) is supplied to the sample 1 from the top head of the probe 3 by the interaction between the magnetic field and the magnet 7a through the probe holding-bar 10. At this moment, the furnace 20 is heated by a current from the temperature controller 21 and then the sample 1 is heated. The heating of the sample 1 is precisely controlled through the predetermined temperature program set in the temperature controller 21. The temperature control may be controlled by the temperature control signal from the CPU 24 which is connected with the furnace 20.

The temperature control can be either heating or cooling, and if necessary, quenching may be done by coupling with appropriate equipment, although such equipment is not specifically shown in the figures.

The degree of the strain (deformation) of the sample 1 at a certain temperature and load (stress) is detected by the detecting circuit 23 through the change of the relative position between the core 5 fixed at the probe holding-bar 10 and the differential transformer 4 set around the core 5. And the signal (from the detecting circuit 23) enters into the CPU 24 and is data-processed therein, and thermomechanical analysis of the sample 1 is performed. A set of the core 5 and the differential transformer 4 can be also called as a differential transformer as well. As this differential transformer is well known, a detailed explanation of the principal of the detection will not be given.

Due to the strain of the sample 1, the probe holding-bar 10 is moved in the direction of its axis with almost certainty and reliability by using the mechanism for horizontally holding the probe holding-bar 10, the mechanism comprising the wires 12, the coil springs 25 and holder rings 11). Therefore, the shift (movement) of the probe holding-bar 10 in the radial direction becomes nil.

As the thermomechanical analyzer of the invention has no balance mechanism as of the prior art, the size of the instrument becomes compact and its assembly becomes very easy. And, even if the deformation of the sample is greater, the instrument can analyze the sample with precision, since the moving range of the probe becomes broader and the degree of the deformation itself can be measured with precision. The linearity between the current inputted to the coil and the force generated by the force generator is improved better, because the change of the gap between the coil and magnet of the force generator is very small.

This application relates to subject matter disclosed in Japanese Application number 4-273024, filed on Oct. 12, 1992, the disclosure of which is incorporated herein by reference.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed:

1. A thermomechanical analyzer for analyzing a sample, comprising:
    a furnace for heating the sample;
    a probe having a longitudinal axis and disposed to contact the sample while the sample is in the furnace so that strain experienced by the sample subjects said probe to movement along said longitudinal axis;
    a probe holding bar fixed vertically to said probe;
    a force generator composed of a magnet and a coil operatively associated with said bar for imposing a force on said probe along said longitudinal axis;
    position detecting means for detecting movement of said probe along said longitudinal axis;
    a holder supporting said force generator; and
    at least one support means connected between said holder and said holding bar for supporting said holding bar in a vertical position by restraining horizontal movement of said holding bar, said support means comprising two bendable wires extending between said holder and said holding bar and lying in a plane generally perpendicular to said longitudinal axis, said wires being angularly offset form one another about said longitudinal axis.

2. An analyzer as defined in claim 1 wherein said support means further comprises a tension spring connected between said holder and said holding bar and angularly offset from each of said wires.

3. An analyzer as defined in claim 2 wherein there are two of said support means spaced apart along said longitudinal axis.

4. An analyzer as defined in claim 1 further comprising: a datum tube for supporting the sample in said furnace; and means for supporting said datum tube for movement parallel to said longitudinal axis relative to said holder.

5. An analyzer as defined in claim 4 further comprising a micrometer coupled to said datum tube for moving said datum tube.

6. An analyzer as defined in claim 1 wherein said position detecting means comprise a differential transformer and a differential transformer core magnetically coupled to said transformer, said core being mounted for movement with said probe.

7. An analyzer as defined in claim 6 wherein said core is fixed to said probe.

8. An analyzer as defined in claim 6 wherein said core is fixed to said holding bar.

* * * * *